US00PP13299P2

(12) United States Plant Patent
Austin

(10) Patent No.: US PP13,299 P2
(45) Date of Patent: Dec. 3, 2002

(54) SHRUB ROSE PLANT NAMED 'AUSRACE'

(75) Inventor: David C. H. Austin, Albrighton (GB)

(73) Assignee: David Austin Roses Limited, Albrighton (GB)

( * ) Notice: Subject to any disclaimer, the term of this patent is extended or adjusted under 35 U.S.C. 154(b) by 13 days.

(21) Appl. No.: 09/641,398

(22) Filed: Aug. 17, 2000

(51) Int. Cl.[7] ..... A01H 5/00
(52) U.S. Cl. ..... Plt./104
(58) Field of Search ..... Plt./104

(56) References Cited

PUBLICATIONS

UPOV–ROM GTITM Computer Database, GTI Jouve Retrieval Software 2001/02, Citations for Ausrace.*

* cited by examiner

*Primary Examiner*—Bruce R. Campell
*Assistant Examiner*—Wendy Couchoud Baker
(74) *Attorney, Agent, or Firm*—Klarquist Sparkman, LLP

(57) ABSTRACT

Shrub rose plant having perfectly rounded, full petaled, fresh tea-scented flowers of a soft creamy yellow that fades to ivory; an attractive, busy growth habit; and high disease resistance.

1 Drawing Sheet

The present invention relates to a new and distinct variety of rose plant of the shrub class which was originated by me by crossing two unnamed seedlings.

The primary objective of this breeding was to produce a new rose variety having a disease-resistant, strongly-growing plant with blooms of an old-fashioned shape that repeat flowers well. The objective was substantially achieved, along with other desirable improvements, as evidenced by the following unique combination of characteristics that are outstanding in the new variety and that distinguish it from its parents, as well as from all other varieties of which I am aware:

1. Fresh tea-scented fragrance;
2. Attractive, bushy growth;
3. Very disease-resistant; and
4. Perfectly rounded, full-petalled flowers of a soft, creamy yellow that fades to ivory.

Asexual reproduction of this new variety by budding, as performed at David Austin Roses Ltd., Bowling Green Lane, Albrighton, England, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) colour chart, except where ordinary dictionary significance of color is indicated.

Parentage:

*Seed parent.*—Unnamed seedling.

*Pollen parent.*—Unnamed seedling.

Classification:

*Botanical.*—*Rosa hybrida.*

*Commercial.*—Shrub rose.

FLOWER

Observations made from specimens grown in a garden environment at Albrighton, England, Jul. 2, 1998 (at age 7)

and Summer 2000. The daily temperature in Albrighton ranges from on average a high in the mid-forties (F) and lows in the low thirties in the winter months to highs in the high sixties and lows near fifty in the summer months. Average monthly duration of bright sunshine ranges from about 180 hours in the summer months to about 50 hours in the winter months.

Blooming habit: Recurrent — Spring and Fall.

Bud:

*Size.*—About ¾ to one inch long when the petals start to unfurl.

*Form.*—Broad based and pointed.

*Color.*—When sepals first divide, the bud color is Yellow Group 11B. When bud is quarter open the upper portion of a petal is Yellow Group 8D, the middle portion is Yellow Group 8C with a base spot of Yellow Group 8B. When half blown, the upper sides of the petals are Yellow Group 8D and Yellow Group 12B (in veins); and the lower sides of the petals are Yellow-Orange Group 19B.

*Sepals.*—Color: Yellow-Green Group 144A with reddish tinge Greyed-Red Group 180A. Surface texture: Hairy edges. There are three normally appendaged sepals. There are two unappendaged sepals with hairy edges.

*Receptacle.*—Color: Yellow-Green Group 144A. Shape: Funnel. Size: Medium; slender (about ¼ to ½ inch). Surface: Smooth.

*Peduncle.*—Length: Medium (averaging about 1.9 inches). Surface: Smooth when young but quickly develops fine prickles. Color: Yellow-Green Group 144B. Strength: Erect.

Bloom:

*Size.*—Medium. Average open size is 2¼ inches.

*Borne.*—Several together in rounded, cupped clusters of four to fourteen blooms.

*Stems.*—Strength Normal. Average length is about two inches.

*Form.*—When first open: Cupped. Permanence: Outer petals curl back.

*Petalage.*—Number of petals under normal conditions: 118.

*Color*.—The upper sides of the petals are White Group 155D on the outer portion, Yellow Group 4D in the middle portion and Yellow Group 12B on the bottom portion. The reverse sides of the petals are White Group 155D, the base being White Group 155A. The major color on the upper side is White Group 155A on the outer petals, and Yellow Group 8D on the inner petals.

*Variegations*.—None.

*Discoloration*.—The general tonality at the end of the first day: Orange Group 27A. At the end of the third day: Orange Group 27D.

*Fragrance*.—Moderate tea-scented.

Petals:

*Texture*.—Thin.

*Shape*.—Round.

*Form*.—Outer petals: Edges slightly quilled. Towards center of flowers: Heavily quilled.

*Arrangement*.—Irregular.

*Persistence*.—Petals hang on and dry.

*Lastingness*.—On the plant: Not tested.

Reproductive parts:

*Anthers*.—Size: Medium. Quantity: Few. Color: Yellow Group 13B. Arrangement: Mixed with petaloids.

*Filaments*.—Color: Yellow Group 7A.

*Pollen*.—Color: Yellow Group 13A.

*Styles*.—Color: Yellow-Green Group 149D.

*Stigmas*.—Color: Yellow Group 3C.

*Hips*.—None produced.

Plant:

*Form*.—Shrub; English.

*Growth*.—Medium. At maturity, height is 3½ feet, width is 2½ feet.

Foliage: Number of leaflets on normal mid-stem leaves: Five.

*Size*.—Medium (4½ to 6½ inches long×4½ to six inches wide).

*Quantity*.—Normal.

*Color*.—New foliage: Upper surface: Yellow-Green Group 146A, overlayed with Greyed-Purple Group 187A especially on edges. Lower surface: Green Group 139C. Old foliage: Upper surface: Yellow-Green Group 147A. Lower surface: Green Group 137C.

Leaflets:

*Shape*.—Elliptic.

*Texture*.—Semi-glossy.

*Edge*.—Serrated.

*Serration*.—Single; small.

*Petiole rachis*.—Color: Yellow-Green Group 145A.

*Petiole underside*.—Smooth; with prickles.

*Stipules*.—Medium (about ¾ inch long).

*Disease resistance*.—Resistant to mildew, blackspot and rust under normal growing conditions.

Wood:

*New wood*.—Color: Yellow-Green Group 146B with Greyed-Purple Group 183B blush. Bark: Smooth.

*Old wood*.—Color: Green Group 137B. Bark: Smooth.

Prickles:

*Quantity*.—On main canes from base: Ordinary. On laterals from main canes: Ordinary.

*Position*.—Quite evenly distributed up the stem.

*Form*.—Concave.

*Color when young*.—Greyed-Red Group 181A.

*Color when mature*.—Brown Group 200D.

Small prickles:

*Quantity*.—On main stalks: None. On laterals: Few.

*Color*.—Greyed-Purple Group 184A.

I claim:

1. A new and distinct variety of rose plant of the shrub class, substantially as herein shown and described, characterized particularly by perfectly rounded, full petaled, fresh tea-scented flowers of a soft creamy yellow that fades to ivory; an attractive, busy growth habit; and high disease resistance.

* * * * *

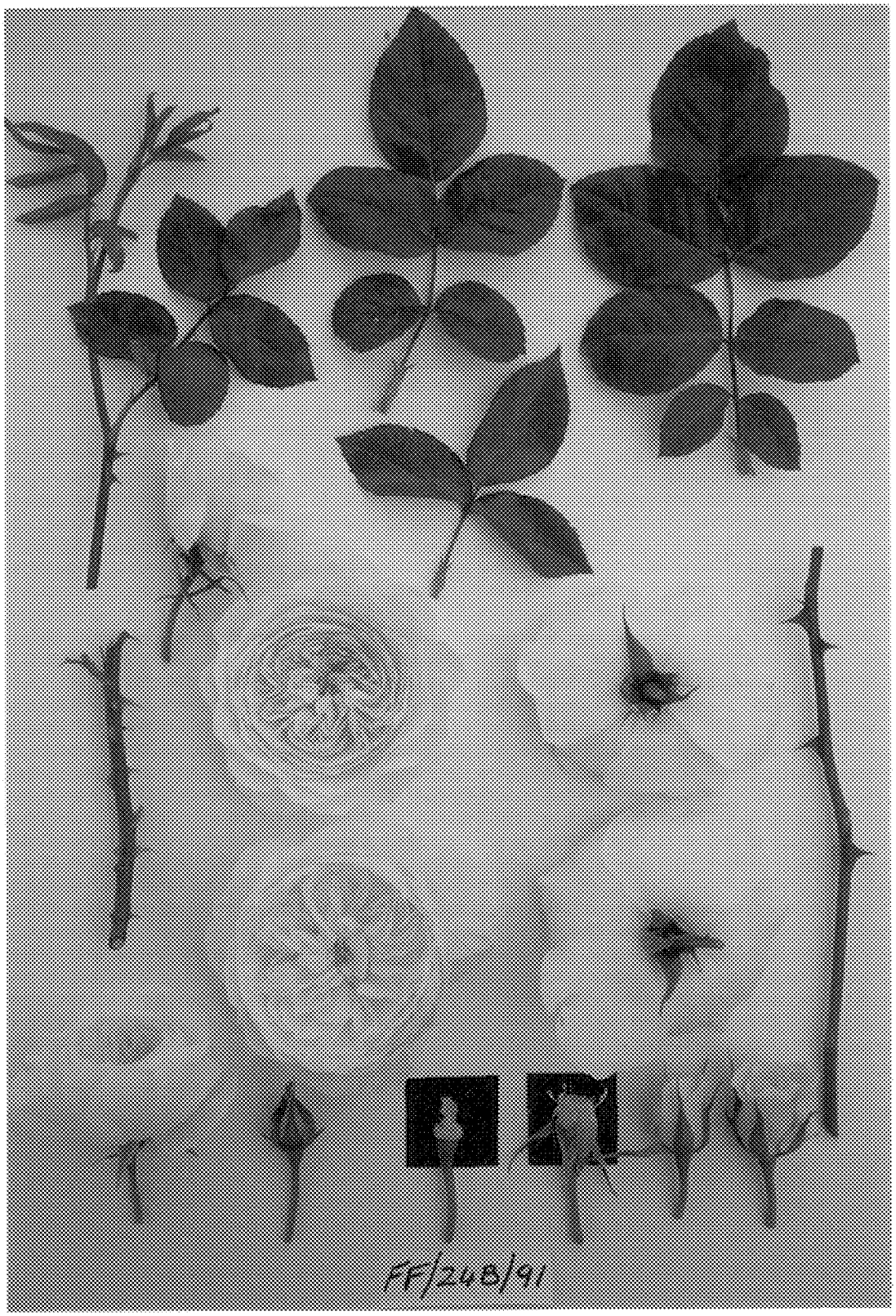
FF/248/91